United States Patent
Harris (10) Patent No.: US 9,333,245 B2
(45) Date of Patent: May 10, 2016

(54) METHODS AND COMPOSITIONS FOR TREATING WOUNDS AND REDUCING THE RISK OF INCISIONAL HERNIAS

(71) Applicant: The Regents of the University of California, Oakland, CA (US)

(72) Inventor: Hobart W. Harris, San Francisco, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 14/383,068

(22) PCT Filed: Mar. 11, 2013

(86) PCT No.: PCT/US2013/030213
§ 371 (c)(1),
(2) Date: Sep. 4, 2014

(87) PCT Pub. No.: WO2013/138238
PCT Pub. Date: Sep. 19, 2013

(65) Prior Publication Data
US 2015/0030678 A1 Jan. 29, 2015

Related U.S. Application Data (60) Provisional application No. 61/609,766, filed on Mar. 12, 2012.

(51) Int. Cl.
*A61K 38/48* (2006.01)
*A61K 38/36* (2006.01)
(Continued)

(52) U.S. Cl.
CPC .............. *A61K 38/4833* (2013.01); *A61K 9/16* (2013.01); *A61K 33/38* (2013.01); *A61K 38/363* (2013.01); *A61L 26/0042* (2013.01);
(Continued)

(58) Field of Classification Search
None
See application file for complete search history.

(56) References Cited

U.S. PATENT DOCUMENTS 5,631,011 A * 5/1997 Wadstrom ...................... 424/400
5,656,035 A * 8/1997 Avoy .............................. 604/191
(Continued)

FOREIGN PATENT DOCUMENTS

WO 9942146 8/1999
WO 0180920 11/2001
(Continued)

OTHER PUBLICATIONS

Hippocrates: Translated by Francis Adams. On Ulcers: Part 7: Written Approximatley 400 B.C.E; English translation by Francis Adams Published in 1849.
(Continued)

*Primary Examiner* — Robert A Wax
*Assistant Examiner* — Melissa Mercier
(74) *Attorney, Agent, or Firm* — Rudy J. Ng; Carol L. Francis; Bozicevic, Field & Francis LLP (57) ABSTRACT

Provided are methods and compositions for treating a wound in a subject. The methods include applying a pharmaceutical composition that includes a first precursor material agent including fibrinogen, a second precursor material agent including thrombin, and silver particles to an abdominal incision site in an amount effective to treat the abdominal incision site. Also provided are pharmaceutical compositions and devices for use in the subject methods.

19 Claims, 3 Drawing Sheets

(51) Int. Cl.
*A61L 26/00* (2006.01)
*A61K 33/38* (2006.01)
*A61K 9/00* (2006.01)
*A61K 9/16* (2006.01)

(52) U.S. Cl.
CPC .......... *A61L 26/0066* (2013.01); *A61K 9/0024* (2013.01); *A61K 9/1611* (2013.01); *A61L 2300/104* (2013.01); *C12Y 304/21005* (2013.01)

(56) References Cited

U.S. PATENT DOCUMENTS

| | | | |
|---|---|---|---|
| 5,752,974 | A | 5/1998 | Rhee et al. |
| 5,827,937 | A | 10/1998 | Agerup |
| 5,962,405 | A | 10/1999 | Seelich |
| 6,719,987 | B2 | 4/2004 | Burrell et al. |
| 6,833,408 | B2 | 12/2004 | Sehl et al. |
| 7,655,257 | B2 | 2/2010 | Peery et al. |
| 7,655,639 | B2 | 2/2010 | Feins |
| 7,963,937 | B2 | 6/2011 | Pauser et al. |
| 2002/0188196 | A1 | 12/2002 | Burbank et al. |
| 2003/0129183 | A1 | 7/2003 | Spillert et al. |
| 2006/0246033 | A1 | 11/2006 | Ninan |
| 2007/0003603 | A1 | 1/2007 | Karandikar et al. |
| 2008/0107744 | A1 | 5/2008 | Chu |
| 2008/0241072 | A1 | 10/2008 | Barry et al. |
| 2008/0254103 | A1 | 10/2008 | Harris et al. |
| 2009/0148502 | A1 | 6/2009 | Pronovost |
| 2010/0080791 | A1 | 4/2010 | Rousseau et al. |
| 2010/0210616 | A1 | 8/2010 | Youngs et al. |
| 2011/0238094 | A1 | 9/2011 | Thomas et al. |
| 2011/0280857 | A1 | 11/2011 | Dowling et al. |

FOREIGN PATENT DOCUMENTS

| | | |
|---|---|---|
| WO | 0197826 | 12/2001 |
| WO | WO 2006026026 A2 * | 3/2006 |
| WO | 2006026026 | 9/2006 |

OTHER PUBLICATIONS

Dubay et al., "The Prevention of Incisional Hernia Formation Using a Delayed-Release Polymer of Basic Fibroblast Growth Factor", Annals of Surgery, 240(1): 179-186 (2004).

El-Khadrawy et al., "Prophylactic prosthetic reinforcement of midline abdominal incisions in high-risk patients", Hernia, 13(3): 267-274 (2009).

Hidalgo et al., "Incisional hernia in patients at risk: can it be prevented?", Hernia, 15(4): 371-375 (2011).

Korenkov et al., "Local administration of TGF-β1 to reinforce the anterior abdominal wall in a rat model of incisional hernia", Hernia, 9(3): 252-258 (2005).

Sierra, J Biomater Appl. 7:309-352 (1993).

Tian et al., "Topical Delivery of Silver Nanoparticles Promotes Wound Healing", ChemMedChem, 2: 129-136 (2007).

Wong et al., Further Evidence of the Anti-inflammatory Effects of Silver Nanoparticles, ChemMedChem, 4: 1129-1135 (2009).

* cited by examiner

METHODS AND COMPOSITIONS FOR TREATING WOUNDS AND REDUCING THE RISK OF INCISIONAL HERNIAS

CROSS-REFERENCE TO RELATED APPLICATION

Pursuant to 35 U.S.C. §119(e), this application claims priority to U.S. Provisional Patent Application Ser. No. 61/609,766, filed Mar. 12, 2012, the disclosure of which is incorporated herein by reference.

INTRODUCTION

Incisional hernias are a frequent complication of abdominal surgery, resulting in considerable patient morbidity and increased health care costs. There are 4-5 million abdominal incisions (laparotomies) performed annually in the United States with hernias resulting after 11-23% of these procedures. Incisional hernias may result in severe morbidity beyond the cosmetic deformity of a visible bulge in the anterior abdominal wall, including intestinal obstruction, bowel ischemia, enterocutaneous fistula and significant limitations on a patient's physical activity and gainful employment. Consequently, there are over 400,000 incisional hernia repairs performed each year making it one of the most common procedures performed by general surgeons. The increase in U.S. health care costs due to incisional hernia repair is estimated to currently exceed eight billion dollars per year, not including the costs of unemployment benefits for this moderately young patient population. Research indicates that incisional hernias result from inadequate or impaired healing of the myofascial abdominal wall following surgery. Accordingly, each of the recognized risk factors for hernia formation inhibits wound healing, including morbid obesity, diabetes, smoking, chronic lung disease, surgical site infection and poor surgical technique. Since the incidence of the major risk factors is increasing, the prevalence of incisional hernias is predicted to increase as well.

Despite the magnitude and significance of the clinical condition, research focused on the prevention of incisional hernias is sparse. While current studies and research efforts are focused on improved repair materials and surgical techniques, the optimal solution to the problem of incisional hernias is prevention.

SUMMARY

Provided are methods and compositions for treating a wound in a subject. The methods include applying a pharmaceutical composition that includes a first precursor material agent including fibrinogen, a second precursor material agent including thrombin, and silver particles to an abdominal incision site in an amount effective to treat the abdominal incision site. Also provided are pharmaceutical compositions and devices for use in the subject methods.

In some embodiments, a method for treating a wound in a subject is provided. The method includes applying a pharmaceutical composition that includes a first precursor material agent including fibrinogen, a second precursor material agent including thrombin, and silver particles to an abdominal incision site in an amount effective to treat the abdominal incision site.

Embodiments of the method may also include that the first precursor material agent, the second precursor material agent and the silver particles are adapted to be combined in situ.

Embodiments of the method may also include that the applying includes applying the first precursor material agent prior to applying the second precursor material agent.

Embodiments of the method may also include that the applying includes applying the second precursor material agent prior to applying the first precursor material agent.

Embodiments of the method may also include that the silver particles are silver microparticles.

Embodiments of the method may also include that the silver particles are spherical.

Embodiments of the method may also include that the silver microparticles have an average diameter of 5 µm or more.

Embodiments of the method may also include that the silver microparticles have an average diameter of 200 µm or more.

Embodiments of the method may also include that the pharmaceutical composition includes 25 mg/mL silver particles.

Embodiments of the method may also include that the pharmaceutical composition includes 250 mg/mL silver particles.

In some embodiments, a pharmaceutical composition for treating a wound in a subject is provided. The pharmaceutical composition includes a fibrin glue and silver particles in an amount effective to treat an abdominal incision site.

Embodiments of the pharmaceutical composition may also include that the silver particles are spherical.

Embodiments of the pharmaceutical composition may also include that the silver particles have an average diameter of 5 µm or more.

Embodiments of the pharmaceutical composition may also include that the silver particles have an average diameter of 200 µm or more.

Embodiments of the pharmaceutical composition may also include that the pharmaceutical composition includes 25 mg/mL silver particles.

Embodiments of the pharmaceutical composition may also include that the pharmaceutical composition includes 250 mg/mL silver particles.

In some embodiments, a device for applying a pharmaceutical composition for treating a wound in a subject is provided. The device includes a sterile container containing a first precursor material agent including fibrinogen, a second precursor material agent including thrombin, and silver particles in an amount effective to treat an abdominal incision site.

Embodiments of the device may also include that the sterile container includes a first chamber containing the first precursor material agent, a second chamber containing the second precursor material agent, and a third chamber containing the silver particles.

Embodiments of the device may also include that the sterile container includes a syringe.

In some embodiments, a kit is provided. The kit includes a sterile container containing a first precursor material agent including fibrinogen, a second precursor material agent including thrombin, and silver particles in an amount effective to treat an abdominal incision site. The kit also includes a sealed package configured to maintain the sterility of the sterile container.

BRIEF DESCRIPTION OF THE FIGURES

FIG. 1 shows graphs of: FIG. 1A, the percentage of clinical incisional hernias in Sprague-Dawley rats (male, 250-300 g) treated with varying doses of silver microparticles versus saline and fibrin glue alone (controls); and FIG. 1B, the anatomic hernia areas with varying doses of silver microparticles and saline and fibrin glue controls, according to embodiments of the present disclosure. Results are mean and standard deviation.

Before the present invention is described in greater detail, it is to be understood that this invention is not limited to the particular embodiments described, and as such may, of course, vary. It is also to be understood that the terminology used herein is for the purpose of describing particular embodiments only, and is not intended to be limiting, since the scope of the present invention is embodied by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. To the extent such publications may set out definitions of a term that conflicts with the explicit or implicit definition of the present disclosure, the definition of the present disclosure controls. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

DETAILED DESCRIPTION

Provided are methods and compositions for treating a wound in a subject. The methods include applying a pharmaceutical composition that includes a first precursor material agent including fibrinogen, a second precursor material agent including thrombin, and silver particles to an abdominal incision site in an amount effective to treat the abdominal incision site. Also provided are pharmaceutical compositions and devices for use in the subject methods.

Below, the subject methods for treating a wound in a subject are described first in greater detail, followed by a review of the compositions and devices that find use in the subject methods, as well as a discussion of various representative applications in which the subject methods, compositions and devices find use.

Methods

Aspects of the present disclosure include a method for treating a wound in a subject. The method includes applying a pharmaceutical composition that includes a first precursor material agent including fibrinogen, a second precursor material agent including thrombin, and silver particles to an abdominal incision site in an amount effective to treat the abdominal incision site. As such, in some cases, treating a wound in a subject includes applying the pharmaceutical composition to a wound in the subject, such as an abdominal incision site in the subject.

By "treatment" or "treating" is meant alleviating, preventing, curing, reducing the occurrence, etc. of a condition in a subject. In some cases, reducing the occurrence includes decreasing the severity and/or incidence of a condition in a subject. In some instances, reducing the occurrence includes reducing the risk of occurrence of a condition in a subject or group of subjects. For example, in a group of subjects, a 50% reduction in the risk of occurrence of a condition means that, on average, the condition is detectable in 50% of the subjects in the group, while the condition is not significantly detectable in the other 50% of the subjects in the group. Percentages may be used when referring to a group of subjects or to an individual subject. In certain instances, the condition includes a hernia, such as an incisional hernia. For example, the incisional hernia may be at an abdominal incision site, such as an abdominal incision site made during a surgical procedure.

In certain instances, treating a wound includes promoting healing of the wound. In some instances, promoting healing of a wound includes an increase in the efficiency of wound healing and/or an increase in the strength of the resulting healed wound site as compared to a wound that has not been treated with the methods and compositions of the present disclosure. In some cases, promoting healing of a wound includes reducing the occurrence of defective wound healing and/or reducing the severity of defective wound healing as compared to a wound that has not been treated with the methods and compositions of the present disclosure. In certain embodiments, the method for treating a wound in a subject reduces the risk of incisional hernia in the subject. By "incisional hernia" is meant a hernia that occurs at an incision site and involves defective or incomplete wound healing at the subcutaneous level (e.g., at the level of the muscle or fascia). In some instances, defective or incomplete wound healing may result in an increased susceptibility to an incisional hernia. By "reduce the risk" is meant that the risk of the occurrence of incisional hernia in a subject treated by the method of the present disclosure is lower that that in a subject that has not been treated by the method of the present disclosure. In some instances, the method reduces the risk of incisional hernia by 30% or more, such as 35% or more, including 40% or more, or 45% or more, or 50% or more, or 55% or more, or 60% or more, or 65% or more, or 70% or more, or 75% or more, or 80% or more, or 85% or more, or 90% or more, or 95% or more, for example by 99% or more. In certain cases, the method reduces the risk of incisional hernia by 60% or more. For example, the method may reduce the risk of a clinical hernia in a subject. By "clinical hernia" is meant a hernia that is observed (e.g., by sight, touch, sound, smell, etc.) during treatment of a patient, rather than determined through laboratory studies. For example, a clinical hernia may be observed as a visible bulge in the abdominal wall.

In certain embodiments, the method for treating a wound in a subject reduces severity of a hernia in a subject should a hernia occur in the subject. In some cases, a reduction in the severity of the hernia corresponds to a reduction in the size of the hernia in the subject. For example, the method may reduce the size of an anatomic hernia in a subject. By "anatomic hernia" is meant a hernia that is detectable by methods other than, or in addition to, clinical observation (e.g., by dissection of the subject, MRI, CT, ultrasound, and the like). The size of an anatomic hernia may be measured by determining the separation between the abdominal muscles (e.g., rectus muscles) at the incision site. For instance, the size of an anatomic hernia may be estimated by multiplying the maximal craniocaudal diameter by the average of two transverse diameter measurements (e.g., approximation of an ellipse). In some instances, the method reduces the size of incisional hernia by 15% or more, such as 20% or more, including 25% or more, or 30% or more, such as 35% or more, including 40% or more, or 45% or more, or 50% or more, or 55% or more, or 60% or more, or 65% or more, or 70% or more, or 75% or more, or 80% or more, or 85% or more, or 90% or more, or 95% or more, for example by 99% or more. In certain cases, the method reduces the risk of incisional hernia by 55% or more.

In certain embodiments, the first precursor material agent, the second precursor material agent and the silver particles are adapted to be combined in situ. For example, the first precursor material agent, the second precursor material agent and the silver particles may be adapted to be combined at the abdominal incision site as the first precursor material agent, the second precursor material agent and the silver particles are applied to the abdominal incision site. Accordingly, in some instances, the method includes combining the first precursor material agent, the second precursor material agent and the silver particles in situ (e.g., at the abdominal incision site). For instance, applying the pharmaceutical composition may include applying the first precursor material agent prior to applying the second precursor material agent. In some cases, the first precursor material agent is applied immediately prior to applying the second precursor material agent. In other cases, applying the pharmaceutical composition includes applying the second precursor material agent prior to applying the first precursor material agent. For example, the second precursor material agent may be applied immediately prior to applying the first precursor material agent. In yet other embodiments, the first and second precursor material agents are applied substantially simultaneously. In still other embodiments, the first and second precursor material agents are combined together to form the pharmaceutical composition prior to applying the pharmaceutical composition to the abdominal incision site. For example, the first and second precursor material agents may be combined together to form the pharmaceutical composition immediately before applying the pharmaceutical composition to the abdominal incision site.

The silver particles may be combined with the first and second precursor material agents at any desired step of the application process. For example, the silver particles may be combined with the first precursor material agent prior to combining the first precursor material agent with the second precursor material agent as described above. In other embodiments, the silver particles may be combined with the second precursor material agent prior to combining the first precursor material agent with the second precursor material agent as described above. In certain other embodiments, the silver particles may be combined with the first and second precursor material agents after combining the first precursor material agent with the second precursor material agent with each other as described above. In certain other embodiments, the first and second precursor material agents and silver particles are combined at substantially the same time. For instance, the first and second precursor material agents and the silver particles may be combined in situ as described above. In yet other embodiments, the silver particles are combined with the first and second precursor material agents to form the pharmaceutical composition prior to applying the pharmaceutical composition to the abdominal incision site. For example, the first and second precursor material agents and silver particles may be combined together to form the pharmaceutical composition immediately before applying the pharmaceutical composition to the abdominal incision site. In yet other embodiments, the silver particles are combines with both the first precursor material agent and the second precursor material agent prior to combining the first and second precursor material agents together to form the pharmaceutical composition.

In certain embodiments, the method includes administering the pharmaceutical composition in an amount effective to treat the abdominal incision site. By "effective amount" is meant a dosage sufficient to cause a significantly detectable effect in the target subject, as desired. In some instances, an effective amount of the pharmaceutical composition is an amount of the pharmaceutical composition sufficient to induce a foreign body reaction in the subject at the site of application. In certain instances, the foreign body reaction includes inflammatory infiltrate consisting of giant cells without epitheliod histiocytes. In certain cases, an effective amount of the pharmaceutical composition includes 10 mg/mL silver particles or more, such as 25 mg/mL silver particles or more, including 50 mg/mL silver particles or more, or 75 mg/mL silver particles or more, or 100 mg/mL silver particles or more, or 150 mg/mL silver particles or more, or 200 mg/mL silver particles or more, or 250 mg/mL silver particles or more, or 300 mg/mL silver particles or more, or 350 mg/mL silver particles or more, or 400 mg/mL silver particles or more, or 450 mg/mL silver particles or more, or 500 mg/mL silver particles or more, or 550 mg/mL silver particles or more, or 600 mg/mL silver particles or more, or 650 mg/mL silver particles or more, or 700 mg/mL silver particles or more, or 750 mg/mL silver particles or more. In certain instances, an effective amount of the pharmaceutical composition includes 50 mg/mL silver particles. In some cases, an effective amount of the pharmaceutical composition includes 500 mg/mL silver particles.

In certain embodiments, an effective amount of the pharmaceutical composition includes a weight/weight ratio of silver particles to fibrinogen of 0.1 (wt/wt) or more, or 0.2 (wt/wt) or more, or 0.3 (wt/wt) or more, or 0.4 (wt/wt) or more, or 0.5 (wt/wt) or more, or 0.6 (wt/wt) or more, or 0.7 (wt/wt) or more, or 0.8 (wt/wt) or more, or 0.9 (wt/wt) or more, or 1 (wt/wt) or more, or 1.1 (wt/wt) or more, or 1.2 (wt/wt) or more, or 1.3 (wt/wt) or more, or 1.4 (wt/wt) or more, or 1.5 (wt/wt) or more, or 1.6 (wt/wt) or more, or 1.7 (wt/wt) or more, or 1.8 (wt/wt) or more, or 1.9 (wt/wt) or more, or 2 (wt/wt) or more, or 2.1 (wt/wt) or more, or 2.2 (wt/wt) or more, or 2.3 (wt/wt) or more, or 2.4 (wt/wt) or more, or 2.5 (wt/wt) or more, or 2.6 (wt/wt) or more, or 2.7 (wt/wt) or more, or 2.8 (wt/wt) or more, or 2.9 (wt/wt) or more, or 3 (wt/wt) or more. For example, an effective amount of the pharmaceutical composition may include a weight/weight ratio of silver particles to fibrinogen of 2.2 (wt/wt) or more.

In certain embodiments, an effective amount of the pharmaceutical composition includes an amount of silver particles, as described herein, applied to a certain wound surface area, such as 0.5 cm$^2$ or more, or 1 cm$^2$ or more, or 2 cm$^2$ or more, or 3 cm$^2$ or more, or 4 cm$^2$ or more, or 5 cm$^2$ or more, or 6 cm$^2$ or more, or 7 cm$^2$ or more, or 8 cm$^2$ or more, or 9 cm$^2$ or more, or 10 cm$^2$ or more, or 11 cm$^2$ or more, or 12 cm$^2$ or more, or 13 cm$^2$ or more, or 14 cm$^2$ or more, or 15 cm$^2$ or more, or 16 cm$^2$ or more, or 17 cm$^2$ or more, or 18 cm$^2$ or more, or 19 cm$^2$ or more, or 20 cm$^2$ or more, or 25 cm$^2$ or more, or 30 cm$^2$ or more, or 35 cm$^2$ or more, or 40 cm$^2$ or more, or 45 cm$^2$ or more, or 50 cm$^2$ or more. For example, an effective amount of the pharmaceutical composition may include an amount of silver particles, such as 250 mg/mL, applied to a wound surface area of 10 cm$^2$ or more. In some instances, an effective amount of the pharmaceutical composition may include an amount of silver particles, such as 2.2 (wt/wt), applied to a wound surface area of 10 cm$^2$ or more.

Pharmaceutical Compositions

Aspects of the present disclosure include a pharmaceutical composition for treating a wound in a subject. In certain embodiments, the pharmaceutical composition includes a fibrin glue and silver particles in an amount effective to treat an abdominal incision site. By "pharmaceutical composition" is meant a composition that includes one or more therapeutic agents used in the prevention, diagnosis, alleviation, treatment, or cure of a disease or condition in a subject (e.g., an animal or human subject).

In certain embodiments, the fibrin glue includes at least a first precursor material agent and a second precursor material agent. The first precursor material agent may include fibrinogen, and the second precursor material agent may include thrombin. Fibrin glue is a biopolymer formed by the addition of thrombin to fibrinogen. Thrombin is an initiator or catalyst that enzymatically cleaves fibrinogen which alters the charge and conformation of the molecule, forming a fibrin monomer. The fibrin monomers then aggregate forming the biopolymer fibrin. After combination of the two thrombin and fibrinogen components, the solution remains liquid for several seconds before polymerizing. Fibrin glue agent, either immediately following mixture of the precursor materials, or by delivering the materials separately to mix in situ, is thus adapted to be delivered to the wound site in the subject via a syringe, catheter or other injectors, thus requiring only a minimally invasive procedure. Fibrin glue is also biocompatible and non-toxic to the subject. Further examples of fibrin glue that may be useful according to various aspects of the present disclosure are described in the following references: Sierra, D H, "Fibrin sealant adhesive systems: a review of their chemistry, material properties and clinical applications." J Biomater Appl. 1993; 7:309-52; and U.S. Pat. No. 5,962,405, the disclosures of each of which are herein incorporated in their entirety by reference. In certain embodiments, the fibrin glue includes additional components, such as, but not limited to, a fibrinolysis inhibitor, albumin (e.g., human albumin), tri-sodium citrate, histidine, niacinamide, polysorbate 80, water (e.g., sterile water, such as water for injection), calcium chloride, sodium chloride, combinations thereof, and the like. For example, the first material precursor agent may include, in addition to fibrinogen, one or more of a fibrinolysis inhibitor, albumin (e.g., human albumin), tri-sodium citrate, histidine, niacinamide, polysorbate 80, water (e.g., sterile water, such as water for injection), and the like. In some instances, the second material precursor agent may include, in addition to thrombin, one or more of albumin (e.g., human albumin), water (e.g., sterile water, such as water for injection), calcium chloride, sodium chloride, and the like. Additional examples of components that may be included in the fibrin glue include, but are not limited to, protease inhibitors, such as aprotinin.

As described above, in certain embodiments, the pharmaceutical composition includes silver particles. The silver particles may be silver microparticles. In some instances, the size of the silver microparticles is sufficient to induce a foreign body reaction in the subject at the site of application. For example, microparticles have an average diameter ranging from 2 μm to 1000 μm. In comparison, nanoparticles have an average diameter of 1 nm to 1000 nm. In some instances, the silver microparticles have an average diameter of 2 μm or more, such as 3 μm or more, including 4 μm or more, or 5 μm or more, or 7 μm or more, or 10 μm or more, or 15 μm or more, or 20 μm or more, or 25 μm or more, or 50 μm or more, or 75 μm or more, or 100 μm or more, or 150 μm or more or 200 μm or more, or 250 μm or more or 500 μm or more. For example, the silver microparticles may have an average diameter ranging from 2 μm to 1000 μm, such as from 2 μm to 750 μm, including from 3 μm to 500 μm, or from 5 μm to 250 μm. In certain instances, the silver microparticles have an average diameter of 5 μm or more. In some cases, the silver microparticles have an average diameter of 200 μm or more. In some embodiments, the silver microparticles include a mixture of silver microparticles having a range of different sizes in the sizes as described above. As used herein, the term "average" is the arithmetic mean.

In certain instances, the silver particles have a substantially symmetrical shape. For example, the silver particles may have a shape that is substantially spherical, elliptical, cylindrical, and the like. In some embodiments, the silver particles have a substantially spherical shape. In other embodiments, the silver particles may have an irregular shape. In certain cases, the silver particles have a substantially smooth outer surface. In other cases, the silver particles have a textured (e.g., rough) outer surface. In some cases, the silver particles include a mixture of silver particles having different shapes and/or textures as described above. In certain instances, the silver particles have a shape and/or texture sufficient to induce a foreign body reaction in the subject at the site of application. For instance, the silver particles may have a spherical shape, a rod shape, a star shape, an irregular shape, combinations thereof, and the like.

In certain embodiments, the pharmaceutical composition includes 10 mg/mL silver particles or more, such as 25 mg/mL silver particles or more, including 50 mg/mL silver particles or more, or 75 mg/mL silver particles or more, or 100 mg/mL silver particles or more, or 150 mg/mL silver particles or more, or 200 mg/mL silver particles or more, or 250 mg/mL silver particles or more, or 300 mg/mL silver particles or more, or 350 mg/mL silver particles or more, or 400 mg/mL silver particles or more, or 450 mg/mL silver particles or more, or 500 mg/mL silver particles or more, or 550 mg/mL silver particles or more, or 600 mg/mL silver particles or more, or 650 mg/mL silver particles or more, or 700 mg/mL silver particles or more, or 750 mg/mL silver particles or more. In certain instances, the pharmaceutical composition includes 50 mg/mL silver particles. In some cases, the pharmaceutical composition includes 500 mg/mL silver particles.

In certain embodiments, the pharmaceutical composition includes a weight/weight ratio of silver particles to fibrinogen of 0.1 (wt/wt) or more, or 0.2 (wt/wt) or more, or 0.3 (wt/wt) or more, or 0.4 (wt/wt) or more, or 0.5 (wt/wt) or more, or 0.6 (wt/wt) or more, or 0.7 (wt/wt) or more, or 0.8 (wt/wt) or more, or 0.9 (wt/wt) or more, or 1 (wt/wt) or more, or 1.1 (wt/wt) or more, or 1.2 (wt/wt) or more, or 1.3 (wt/wt) or more, or 1.4 (wt/wt) or more, or 1.5 (wt/wt) or more, or 1.6 (wt/wt) or more, or 1.7 (wt/wt) or more, or 1.8 (wt/wt) or more, or 1.9 (wt/wt) or more, or 2 (wt/wt) or more, or 2.1 (wt/wt) or more, or 2.2 (wt/wt) or more, or 2.3 (wt/wt) or more, or 2.4 (wt/wt) or more, or 2.5 (wt/wt) or more, or 2.6 (wt/wt) or more, or 2.7 (wt/wt) or more, or 2.8 (wt/wt) or more, or 2.9 (wt/wt) or more, or 3 (wt/wt) or more. For example, the pharmaceutical composition may include a weight/weight ratio of silver particles to fibrinogen of 2.2 (wt/wt) or more.

In certain embodiments, the pharmaceutical composition includes an amount of silver particles, as described herein, applied to a certain wound surface area, such as 0.5 $cm^2$ or more, or 1 $cm^2$ or more, or 2 $cm^2$ or more, or 3 $cm^2$ or more, or 4 $cm^2$ or more, or 5 $cm^2$ or more, or 6 $cm^2$ or more, or 7 $cm^2$ or more, or 8 $cm^2$ or more, or 9 $cm^2$ or more, or 10 $cm^2$ or more, or 11 $cm^2$ or more, or 12 $cm^2$ or more, or 13 $cm^2$ or more, or 14 $cm^2$ or more, or 15 $cm^2$ or more, or 16 $cm^2$ or more, or 17 $cm^2$ or more, or 18 $cm^2$ or more, or 19 $cm^2$ or more, or 20 $cm^2$ or more, or 25 $cm^2$ or more, or 30 $cm^2$ or more, or 35 $cm^2$ or more, or 40 $cm^2$ or more, or 45 $cm^2$ or more, or 50 $cm^2$ or more. For example, the pharmaceutical composition may include an amount of silver particles, such as 250 mg/mL, applied to a wound surface area of 10 $cm^2$ or more. Other amounts of silver particles per wound surface area may be used, such as any of a variety of mg/mL of silver particles described herein applied to any of a variety of wound surface areas as described herein. In some instances, the pharmaceutical composition may include an amount of silver particles, such as 2.2 (wt/wt), applied to a wound surface area of 10 $cm^2$ or more.

In certain embodiments, the silver particles are substantially solid. Substantially solid particles may, in some instances, be porous (e.g., micro-porous, nano-porous, etc.). However, substantially solid particles do not encompass hollow particles that have a void space surrounded by shell. In these embodiments, the silver particles do not include hollow particles. In certain instances, the silver particles do not include a polymeric material. For example, the silver particles may include only silver (e.g., silver, silver oxide, silver ions, etc.).

Devices

Aspects of the present disclosure include a device for applying a pharmaceutical composition for treating a wound in a subject. The device includes a sterile container containing a first precursor material agent including fibrinogen, a second precursor material agent including thrombin, and silver particles in an amount effective to treat an abdominal incision site. By "sterile" is meant that there are substantially no microbes (such as fungi, bacteria, viruses, spore forms, etc.).

In certain embodiments, the sterile container is configured to maintain the first and second precursor material agents in separate chambers during storage and until use. In some cases, the sterile container includes two or more chambers that include the precursor material agents for fibrin glue. For example, the sterile container may include a first chamber that includes a first precursor material agent (e.g., fibrinogen) and a second chamber that includes a second precursor material agent, (e.g., thrombin). The first and second chambers may be separate chambers that do not allow the first and second precursor material agents to contact each other until use.

In some instances, the sterile container is configured to maintain the first and second precursor material agents and the silver particles in separate chambers during storage and until use. For example, the sterile container may include first and second chambers as described above, and a third chamber that contains silver particles. The silver particles may be provided in an appropriate solvent. For instance, the silver particles may be provided in a solvent, such as, but not limited to, water, a solution (e.g., calcium chloride solution), a buffer, and the like. The first, second and third chambers may be separate chambers that do not allow the first and second precursor material agents and the silver particles to contact each other until use.

In some cases, the sterile container includes a nozzle. The nozzle may be in fluid communication with the two or more chambers of the sterile container. For example, the nozzle may be in fluid communication with the first, second and third chambers as described above. In some embodiments, the sterile container is configured to dispense the first precursor material agent, the second precursor material agent and the silver particles through a single nozzle. In these embodiments, the sterile container may be configured to mix the first precursor material agent, the second precursor material agent and the silver particles as the first precursor material agent, the second precursor material agent and the silver particles are dispensed from the sterile container through the nozzle. Embodiments of the sterile container that include a nozzle as described above may facilitate the in situ mixture and application of the first precursor material agent, the second precursor material agent and the silver particles to an abdominal incision site.

In certain embodiments, the sterile container includes a syringe. The syringe may include a first chamber, a second chamber and a third chamber as described above. For example, the syringe may be configured as a three-barreled syringe with each separate barrel containing one of the first precursor material agent, the second precursor material agent or the silver particles.

Embodiments of the device for applying a pharmaceutical composition for treating a wound in a subject may also include other types of devices suitably adapted for applying the pharmaceutical composition to the subject. For example, the device may include a pressurized container. The pressurized container may include one or more chambers as described above (e.g., a first chamber, a second chamber, a third chamber, etc.). The pressurized container may be configured to maintain the contents of the one or more chambers at a pressure greater than standard atmospheric pressure. In some instances, the pressurized container includes a valve, and may be configured to dispense the contents of the one or more chambers when the valve is in an open position thereby allowing the pressurized contents of the container to be released from the container. For example, the pressurized container may be configured as a spray container (e.g., a pump handle spray container), an aerosol container, and the like.

Utility

The subject methods and compositions find use in a variety of different applications where the treatment of a wound in a subject is desired. In some instances, the wound may be a chronic wound, such as an ulcer (e.g., a pressure ulcer, a diabetic foot ulcer, and the like). In certain cases, the wound may be a surgical wound or a trauma wound, such as, but not limited to, a surgical or traumatic soft tissue wound (e.g., a surgical or traumatic muscle wound, a surgical or traumatic fascia wound, etc.).

For example, the wound may be a wound at an incision site in a subject, such as an abdominal incision site. In certain embodiments, the methods and compositions find use in the treatment of a wound in a subject, where the treatment includes promoting healing of the wound in the subject. The subject methods and compositions also find use in the prevention or reduction in the risk of occurrence of undesired side effects associated with a wound in a subject. For example, the subject compositions find use as a therapeutic agent indicated for prophylactic use in the prevention and/or reduction in the risk of occurrence of undesired side effects associated with a wound, such as an abdominal incision site. Thus, the subject methods and compositions find use in abdominal surgery protocols to promote healing of an abdominal incision site in a subject.

Kits

Also provided are kits that find use in practicing the subject methods, as described above. For example, kits for practicing the subject methods may include a sterile container containing a first precursor material agent, a second precursor material agent, and silver particles in an amount effective to promote healing at an abdominal incision site. As described above, the first precursor material agent may include fibrinogen and the second precursor material agent may include thrombin. In certain embodiments, the kits include a sealed package configured to maintain the sterility of the sterile container. The sealed package may be sealed such that substantially no external contaminants, such as dirt, microbes (e.g., fungi, bacteria, viruses, spore forms, etc.), liquids, gases, and the like, are able to enter the sealed package. For example, the sealed package may be sealed such the package is water-tight and/or air-tight.

In certain embodiments, the kit may include one or more separate containers. The one or more separate containers may each include a different component of the pharmaceutical composition, such as the first precursor material agent in a first container, a second precursor material agent in a second container, and silver particles in a third container. The one or more containers may be provided as separate individual containers, or may be connected or formed together as a single unit. In some cases, the containers are configured to be frozen during storage. In certain instances, the containers are configured to contain a lyophilized component, such as the first precursor material agent or the second precursor material agent. For example, the container may be a vial, a bottle, and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Methods

Animal Models

All procedures were performed with the prior approval of the University of California, San Francisco Institutional Animal Care and Use Committee. The animals were acclimated to laboratory conditions for a minimum of 5 days before undergoing surgery and provided access to water and standard rat chow ad libitum.

Incisional Hernia Model

Sprague-Dawley rats (male, 250-300 g, Charles River, Cambridge, Mass.) underwent an established incisional hernia model procedure, where >80% of the animals develop incisional hernias within 28 days. The animals were placed under isoflurane anesthesia, the ventral abdominal wall hair shaved with electric clippers and the surgical field prepared with 70% alcohol. A 6-cm×3-cm, rectangular, full-thickness skin flap based 2 cm lateral to the ventral midline was raised through the avascular prefascial plane, thereby separating the skin incision from the underlying fascial wound-healing environment. The 1:2 ratio of flap length to width was maintained to prevent ischemia of the skin flap. A 5-cm midline laparotomy incision was made, the intestines manipulated and then the myofascial incision closed with 2 interrupted 5-0 plain catgut (rapidly absorbable) sutures placed 5 mm from the cut myofascial edges and one-third the distance from the cranial and caudal ends of the midline laparotomy incision, respectively, before the skin flap was closed with a continuous 4-0 vicryl suture to prevent intestinal evisceration. Immediately after the surgery, 0.4 ml of bupivacaine 0.25% was infused subcutaneously around the abdominal incision and the rats were observed every 2 minutes until they awoke and resumed normal activity. The rats were returned to individual cages and monitored twice daily. At 12 and 18 hours post-operation, 0.05 mg/kg buprenorphine was injected subcutaneously.

Modified Incisional Hernia Model

Sprague-Dawley rats (male, 250-300 g) underwent a modified incisional hernia model where the animals were placed under isoflurane anesthesia and the ventral abdominal wall prepared and opened as described above. In these animals, the 5-cm, full-thickness, midline laparotomy incision was closed with a continuous 4-0 vicryl suture placed 5 mm from the cut myofascial edges to promote normal wound healing. The skin closure and post-surgical management of the animals was identical to that previously described.

Study Designs

Prevention of Incisional Hernias

The first set of experiments was performed to determine whether a combination of silver metal microparticles and fibrin glue could reduce the risk of occurrence of incisional hernias in rats using an established experimental model. In the experiments described herein, three dosages of silver microparticles (0, 25, and 250 mg/ml) were administered in combination with sterile fibrin glue (TISSEEL®, Baxter Healthcare Corp., Hayward, Calif.). These dosages were approximately 10- to 100-fold lower than the chronic oral reference dose (RfD) for orally administered silver in humans. Silver microparticles with an average diameter of 250 µm were used.

Fifty-three animals were randomly assigned to each of two treatment groups and two control groups, saline and fibrin glue (vehicle) alone. Animals in the treatment groups had either 25 mg/ml (low-dose) or 250 mg/ml (high-dose) silver microparticles dispersed in fibrin glue (0.1 ml applied per cm$^2$ of the myofascial incision) topically applied to the sutured myofascial incisions before skin closure. Animals in the control groups had an equal volume of either sterile saline (0.5 ml) or fibrin glue alone applied to their sutured myofascial incisions before skin closure. For the treatment groups, the fibrin glue was mixed with apyrogenic silver microparticles (Sigma Chemicals, St. Louis, Mo.) at the time of topical administration. On day 28 all animals were euthanized by anesthetic overdose and bilateral thoracotomy, the entire ventral abdominal wall excised and the skin separated from the myofascial tissue. The abdominal wall muscle was photographed and evaluated for the presence of a hernia defect, and sections of tissue that included the wound-healing interface along with normal adjacent tissue were immediately fixed in 10% neutral-buffered formalin in preparation for histology. Biopsies were taken of the muscle-hernia/healing incision interface and frozen in liquid nitrogen for collagen mRNA analysis. Rats with a visible bulge in the abdominal wall prior to euthanasia were classified as having a clinical hernia. Once the abdominal wall was excised, it was carefully examined for visible separation between the rectus muscles. If present, the total area of separation was estimated by multiplying the maximal craniocaudal diameter×the average of two transverse diameter measurements (e.g., approximation of an ellipse) and classified as an anatomic hernia.

Additional experiments were conducted to determine whether the combination of another type of metal microparticles (gold) and fibrin glue, or silver metal microparticles and another natural protein matrix (Matrigel™) had the same effect on preventing incisional hernias in rats using the same experimental model described above. In this set of experiments described herein, three dosages of gold microparticles were administered in combination with sterile fibrin glue (0, 25, and 250 mg/ml gold microparticles dispersed in TISSEEL® with 0.1 ml applied per cm$^2$ of the myofascial incision). These dosages were the same as used in the experiments involving silver metal microparticles above. Gold microparticles with an average diameter of 45 µm were used.

Thirty-two animals were randomly assigned to each of two treatment groups and received either 25 mg/ml (low-dose) or 250 mg/ml (high-dose) gold microparticles dispersed in fibrin glue (0.1 ml applied per cm$^2$ of the myofascial incision) topically applied to the sutured myofascial incisions before skin closure. The fibrin glue was mixed with apyrogenic gold microparticles (Sigma Chemicals) at the time of topical administration. On day 28 all animals were euthanized by anesthetic overdose and bilateral thoracotomy, the entire ventral abdominal wall excised and the skin separated from the myofascial tissue. The animals were evaluated as described above.

An additional twenty-five animals were randomly assigned to each of three treatment groups receiving either 0, 25 mg/ml (low-dose) or 250 mg/ml (high-dose) silver microparticles dispersed in Matrigel™ (BD Biosciences, San Jose, Calif., 0.1 ml applied per cm$^2$ of the myofascial incision) topically applied to the sutured myofascial incisions before skin closure. The Matrigel™ was mixed with silver microparticles at the time of topical administration. On day 28 all animals were euthanized by anesthetic overdose and bilateral thoracotomy, the entire ventral abdominal wall excised, skin separated from the myofascial tissue and the animals evaluated as previously described.

Normal Myofascial Wound Healing

A second set of experiments was performed to determine the effect of silver microparticles on normal myofascial wound healing, as measured by the tensile strength, histology and collagen I gene expression of the incision, using a modified incisional hernia model.

Sixty animals were randomly assigned to each of two treatment groups and two control groups (saline or fibrin glue alone) before closing the skin flap with a continuous 4-0 vicryl suture. Animals in the treatment groups had either low- or high-dose silver microparticles combined with fibrin glue (1 ml/10 cm$^2$ or 0.5 ml/5-cm myofascial incision) topically applied to their sutured myofascial incisions before skin closure, covering a total surface area of 5 cm$^2$. Animals in the control groups had either an equal volume of sterile saline (0.5 ml) or fibrin glue applied to their sutured myofascial incisions before skin closure. On day 28, all of the animals were euthanized, the ventral abdominal wall excised, and the skin separated from the myofascial tissue. The fascial sutures were removed and two fascial strips measuring 5-cm×2-cm (transverse×craniocaudal orientation) were cut from each resected abdominal wall using a cutting template to minimize variability between the resected specimens. The fascial strips then underwent tensiometric mechanical analysis. Additional muscle tissue that included the muscle-healing incision interface was taken for histology along with biopsies that were frozen in liquid nitrogen for collagen analysis.

Histology

Fresh biopsies of the abdominal wall fascia-fascia interface were fixed in formalin, embedded in paraffin, sectioned, and stained with hematoxylin and eosin or trichrome. An independent pathologist blinded to the different treatment groups analyzed tissue sections.

Collagen, Inflammatory Cytokine, and Growth Factor mRNA Expression mRNA expression of collagen (types I and III), inflammatory cytokines (interleukin (IL)-1, IL-6, tumor necrosis factor (TNF-α), and growth factors specific for wound healing (transforming growth factor (TGF-β), platelet derived growth factor (PDGF), vascular endothelial growth factor (VEGF), fibroblast growth factor (FGF), and insulin-like growth factor (IGF)) were analyzed using reverse transcriptase-PCR. Total RNA was extracted from homogenized fascial specimens using TRIZOL reagent. After extraction with chloroform and isopropanol precipitation, the RNA pellet was washed with 75% ethanol and then resuspended in 40.5 μL of diethylpyrocarbonate (DEPC)-treated water. One microliter of the RNA solution was then taken for spectrophotometric verification of RNA presence using the NanoDrop 1000 (Thermo-Scientific, Wilmington, Del.). All reverse transcript (RT) reactions were performed simultaneously using a master mix to eliminate variability and ensure fidelity of RT efficiency. cDNA was synthesized using the GeneAmp RNA PCR Kit (Applied Biosystems, Foster City, Calif.) in 20 μL volumes, which contained less than 1 μg of total RNA, 2.504 of random hexamers, 1 U/μL of RNase Inhibitor, 1 mM of each dNTP, 5 mM of $MgCl_2$ solution, and 2.5 U/μL of murine leukemia virus reverse transcriptase. This reaction was incubated at 42° C. for 15 minutes, 99° C. for 5 minutes, and 5° C. for 5 minutes. Collagen I and III, IL-1, IL-6, TNF-α, TGF-β, PDGF, VEGF, FGF, IGF, and glyceraldehyde-3-phosphate dehydrogenase (GAPDH) primers were designed using conserved sequences from published GenBank complete and partial mRNA sequences of various species. Primers used were: Col1 Fwd: CGGTGGTTATGACTTCAGCTTC; Col1 Rev: TCAGGCTCTTGAGGGTAGTGTC; Col3 Fwd: GGTCCTGCAGGTAACAGTGGT; Col3 Rev: CATCAC-CTTTTGGTCCAGCTAC; IL-1 Fwd: ACAATGAGTGA-CACTGCCTTCC; IL-1 Rev: AGCATCCAGCT-TCAAATCTCAC; IL-6 Fwd: AAGCACAAATAGTGCCCAGTG; IL-6 Rev: TGTACT-CAGGCTCACAGAGCAG; TNF-α Fwd: CAGCA-GATGGGCTGTACCTTAT; TNF-a Rev: CCTTGTCCCT-TGAAGAGAACCT; TGF-β Fwd: GACATGAACCGACCCTTCCT; TGF-b Rev: TAGTTGG-TATCCAGGGCTCTCC; PDGF Fwd: CAAGACCAG-GACGGTCATTTAC; PDGF Rev: GATCAAGAAGTTG-GCCGATGT; VEGF Fwd: ACGTCTACCAGCGCAGCTATT; VEGF Rev: ATCGGGG-TACTCCTGGAAGAT; FGF Fwd: TGTTGGTCACA-CAAGCGTAGAG; FGF Rev: ATGATGTGCAGAGCAT-CAACTG; IGF Fwd: ATTGTGGATGAGTGTTGCTTCC; IGF Rev: GTACATCTCCAGCCTCCTCAGA; GAPDH Fwd: GTTACCAGGGCTGCCTTCTC; GAPDH Rev: GGGTTTCCCGTTGATGACC. PCR amplification was conducted in a total of 5 μl with the following components: 2.5 μl of 2× Power Sybr Green Master Mix (Applied Biosystems), 1.0 μl of 0.2 μm primer (forward+reverse), 1.0 μl of DNA (10 ng for the first test, 1:10 dilution for the second test), and 0.5 μl of $dH_2O$. The amplification reactions were conducted in 60 sequential cycles of 95° C. for 10 minutes, 95° C. for 15 seconds, and 60° C. for 1 minute reactions on a 7900HT instrument (Applied Biosystems). PCR products were digitally analyzed in real time to determine the fluorescence intensity by calculating the Ct value for each curve, and quantified using the Delta-Delta Ct calculation method.

Tensiometric Analysis

Mechanical testing of the abdominal wall fascial strips was performed within 4 h of necropsy. Breaking strength analysis of the fascia-fascia interface was performed using an Instron Tensiometer (model MicroTester®; Instron Corporation, Canton, Mass.) set at a crosshead speed of 10 mm/min. Breaking strength was defined as the force in Newtons required to rupture the healed myofascial incision for each fascial strip. The fascial strips were mounted into the load frame via pneumatic graspers, preloaded to 0.1 Newtons with the gauge length measured between the grips. The load frame applied testing loads to the fascial strips until mechanical tissue disruption occurred. Force and tissue deformation data was simultaneously captured via computer and data analysis performed using Bluehill® Software (Instron Corporation).

Statistical Analysis

Student's t test was used to determine differences in tensiometric mechanical measurements. The Fischer exact test was used to determine differences in the incidence of incisional hernias. Values are reported as the mean±standard deviation. P values of <0.05 were considered significant.

Results

Prevention of Incisional Hernias

Figure 1:
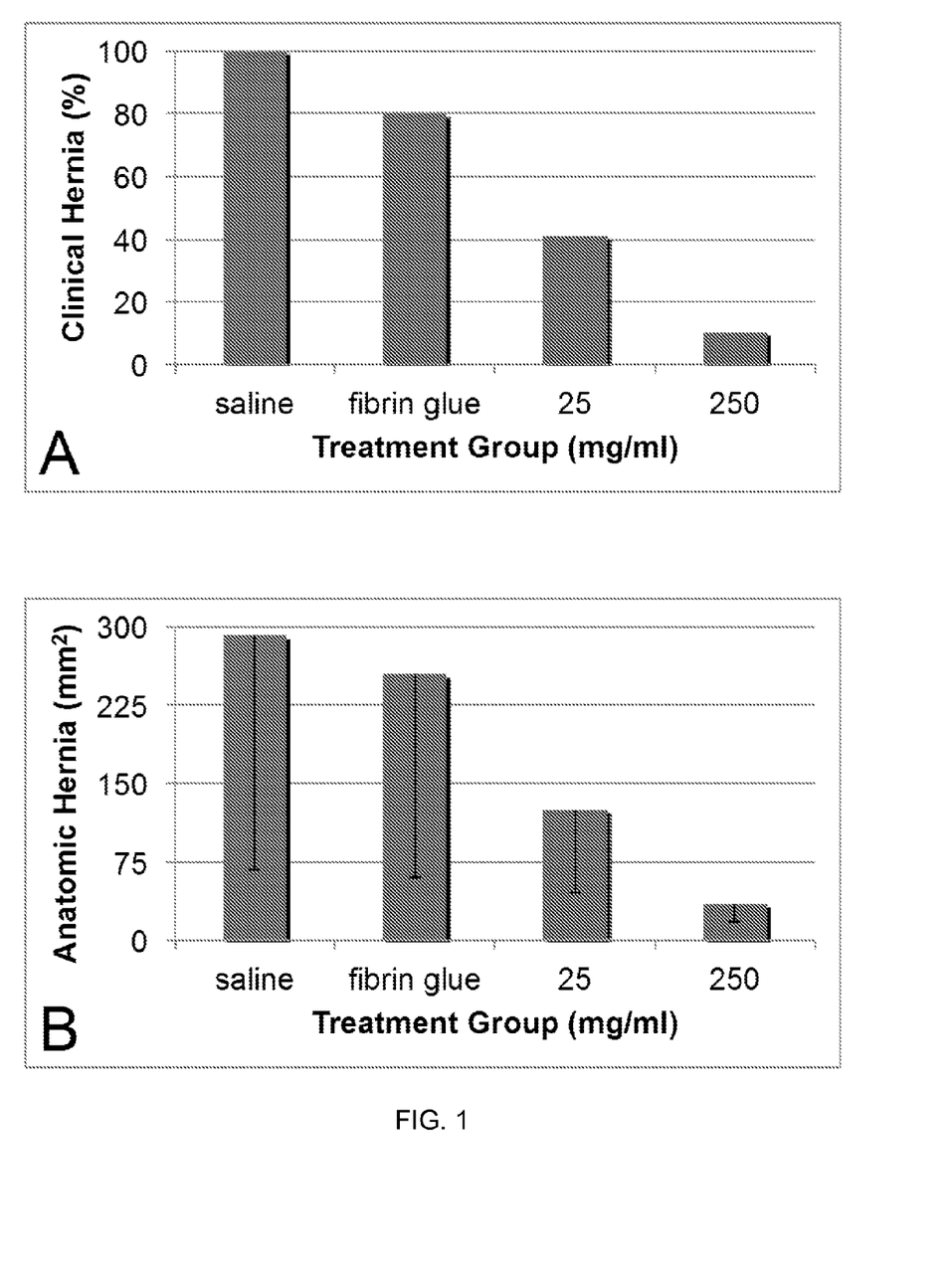
Figure 2:
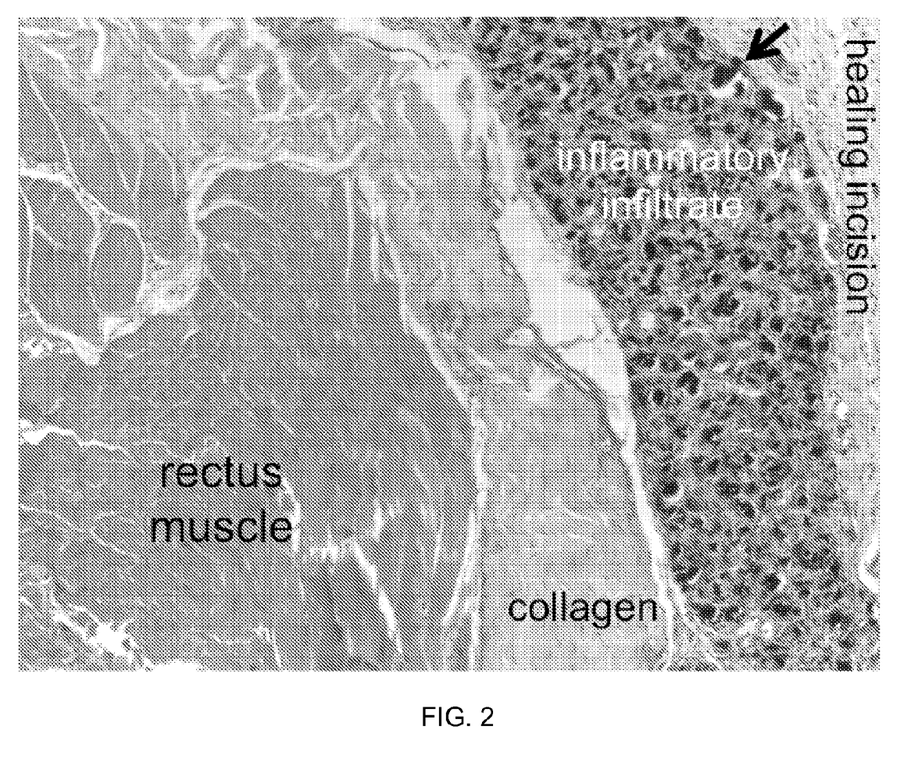
FIG. 2 shows a photomicrograph of a hematoxylin-eosin stained cross-section of a silver-treated healing fascial incision on postoperative day 28, which revealed silver microparticles, a foreign body reaction (e.g., inflammatory infiltrate consisting of giant cells without epitheliod histiocytes), and early wound fibrosis consisting of collagen fibers and no true granulomas (40× magnification), according to embodiments of the present disclosure.

Treatment with silver microparticles significantly reduced the formation of incisional hernias in rats. Clinical hernias developed after 28 days in 100% of saline-treated and 65% of fibrin glue-treated controls compared to 41% and 11% of rats treated with low- and high-dose silver microparticles, respectively ($p<0.05$; FIG. 1A). Similarly, low- and high-dose silver microparticles significantly reduced the size of anatomic hernias in rats after 28 days by 57% and 88%, respectively ($p<0.05$; FIG. 1B). Fibrin glue alone reduced the incidence of clinical hernias by 35% and anatomic hernia size by 16%. Histology of silver-treated myofascial incisions in cross-section reliably demonstrated three distinct, concentric zones of tissue. In the center of the healing incision were microparticles (indicated by the arrow) within a nongranulomatous inflammatory infiltrate, adjacent to a zone of newly synthesized collagen, next to rectus abdominis (skeletal) muscle (FIG. 2). There was no significant difference in collagen 1 or 3, cytokine or growth factor gene expression at the muscle-hernia/healing incision interface between the different experimental groups at the 28-day time point (data not shown). Treating myofascial incisions with silver metal microparticles after suture closure augmented wound healing and thus decreased the rate of incisional hernia formation.

Normal Myofascial Wound Healing

Silver microparticles had no significant effect on normal myofascial wound healing in rats after 28 days. Tensiometric analysis of abdominal wall fascial strips from all experimental groups revealed no significant difference in relative tensile strengths (saline: 16.4±6.8 N, fibrin glue alone: 12.7±5.3 N, low-dose: 15.6±5.3 N, high-dose: 13.0±4.6 N; $p>0.4$). Similarly, there was no significant difference in histology or gene expression between the experimental groups (data not shown).

Discussion

The topical application of silver microparticles in fibrin glue to midline laparotomies significantly reduced the development of incisional hernias in a dose-dependent manner. Low-dose (25 mg/ml) and high-dose (250 mg/ml) silver decreased the incidence of hernias by approximately 59% and 89%, respectively. Also, the two dosages of silver microparticles reduced the average size of the hernia defects that developed to a similar degree. Histology of the healing laparotomies revealed the formation of three distinct zones of tissue concentrically arranged around the wound. Localized in the center zone were the silver microparticles that appeared embedded within a non-granulomatous, foreign body reaction (inflammatory infiltrate) containing multinucleated giant cells. Adjacent to the center zone was an area of early fibrosis composed of fibroblasts and maturing collagen fibers. The third and outermost zone consisted of rectus abdominis muscle. The wound histology revealed that the microparticles were concentrated in the middle of the healing incision where they appeared to induce a foreign body reaction, including collagen and early fibrosis, which bridged the gap separating the medial borders of the rectus muscles. The silver microparticle treatment decreased incisional hernia formation. However, silver microparticle treatment was not associated with a dose-dependent increase in collagen, cytokine or growth factor gene activity at the 28-day time point. Since these genes are normally expected to be quiescent four weeks after wounding, the silver microparticle treatment did not result in a prolonged change in gene expression. The topical application of fibrin glue without silver microparticles to midline laparotomies reduced the development of clinical and anatomic incisional hernias by 16-35%. The histology analysis in this group showed that fibrin glue alone induced a foreign body reaction, however to a lesser degree than the foreign body reaction induced by the silver microparticles. While less significant than the foreign body reaction induced by the silver microparticles, these data indicated a direct, mechanistic correlation between the induction of a foreign body reaction and the prevention of incisional hernias.

Silver microparticles had no measured effect on the histology, gene expression or tensile strength of normally healing abdominal incisions. Generally, one would predict that silver microparticles alone would increase the fibrotic healing response under all circumstances, and that silver treatment alone would not only reduce incisional hernia formation, but also increase the strength of a normally healing wound. Unexpectedly, as shown in the experiments discussed above, the silver microparticles improved myofascial wound healing under conditions in an impaired wound healing model while having no significant adverse effects (such as excessive scarring) in a normal wound healing model. Without being limited to any particular theory, in certain embodiments, the mechanism by which silver improves myofascial wound healing may be associated with the development of a foreign body reaction to the silver metal particles.

As shown in the experiments discussed above, treatment with silver particles alone had no measured effect as described above. Treatment with fibrin glue alone reduced the incidence of clinical hernias by 35% and anatomic hernia size by 16%. However, fibrin glue with silver particles reduced the incidence of clinical hernias by 59% and 89% in rats treated with the low- and high-dose silver microparticles, respectively, and reduced the size of anatomic hernias by 57% and 88% in rats treated with the low- and high-dose silver microparticles, respectively. Thus, treatment with fibrin glue with silver microparticles showed an effect that was not merely additive in reducing both the incidence of clinical hernias and the size of anatomic hernias as compared to the administration of silver particles alone or fibrin glue alone.

The experiments discussed above that included treatment with gold particles dispersed in fibrin glue showed no measured effect on reducing the incidence of clinical hernia. In addition, the experiments discussed above that included treatment with silver particles dispersed in a natural protein matrix (Matrigel™) also showed no measured effect on reducing the incidence of clinical hernia. Thus, treatment with fibrin glue with silver microparticles reduced both the incidence of clinical hernias and the size of anatomic hernias as compared to the administration of gold particles in fibrin glue or silver particles in a natural protein matrix (Matrigel™).

Example 2

Experiments were performed using a diabetic mouse wound healing model to test the efficacy of compositions of the present disclosure as compared to a negative control.

All procedures were performed with the prior approval of the University of California, San Francisco Institutional Animal Care and Use Committee. Genetically diabetic C57BL/KsJ-db/db mice were obtained from Jackson Laboratories (Bar Harbor, Me.) and were between 8-10 weeks of age at the time of testing. The animals were acclimated to laboratory conditions for a minimum of 2 days prior to undergoing surgery and all were provided access to water and standard rat chow ad libitum.

Mice were placed under isoflurane anesthesia and the dorsum was shaved with electrical clippers. 0.1 ml of 1/30 dilution of 0.3 mg/ml buprenorphine was injected subcutaneously, then the dorsum was prepared with betadine antiseptic solution. A 2.0 cm diameter circle was traced on the prepared area. 0.5 ml of bupivacaine (0.25%) was injected around the perimeter of the tracing for local analgesia. The traced circular area was then excised including the panniculus carnosus layer. Each animal had their wound traced on individual clear plastic sheets for weekly tracings, and then animals were then randomly assigned into either a control group (n=19) or an experimental group (n=33). Approximately 0.2 to 0.3 ml of saline was applied to the open wounds on the control mice, and Composition A was topically applied to the wounds on the experimental mice. Composition A included silver microparticles dispersed in fibrin glue (250 μm average diameter at a concentration of 250 mg/ml in fibrin glue with 0.1 ml applied per $cm^2$ of the open wound). The mice were then returned to individual cages and allowed to awaken and resume normal activity. The mice were examined at weekly intervals and the healing wound was traced on the clear plastic sheets each week until the eschar fell off, indicating that the underlying wound had healed. After the wounds had epithelialized, the mice were euthanized by anesthetic overdose and bilateral thoracotomy, and the healed tissue was excised for histochemical analysis. The areas from the wound tracing were measured using an imaging program, Image J.

Statistical analysis on wound size (e.g., area of the wound) was performed comparing the mean values from the control and experimental groups using a Student t-test calculator (GraphPad Software, La Jolla, Calif.).

Figure 3:
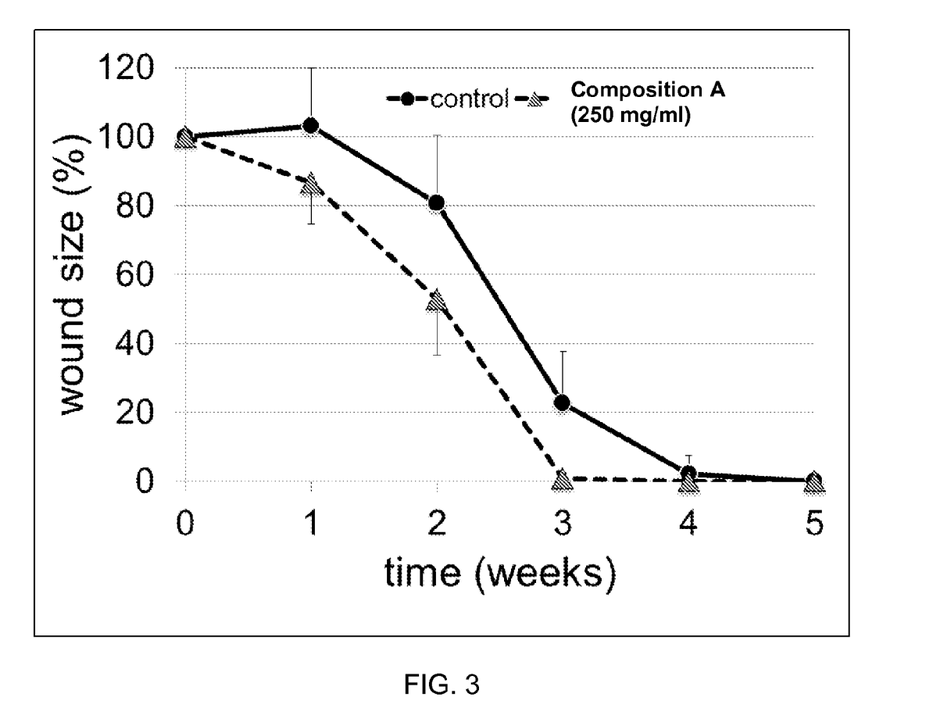
FIG. 3 shows a graph of wound size (%) vs. time (weeks) for diabetic mouse wound healing experiments for compositions of the present disclosure as compared to a negative control, according to embodiments of the present disclosure.

The results are shown in Table 1 and FIG. 3.

TABLE 1

| Time (weeks) | Wound Size, % (control group) | Wound Size, % (experimental group) | Standard Deviation (control group) | Standard Deviation (experimental group) |
| --- | --- | --- | --- | --- |
| 0 | 100.0 | 100.0 | — | — |
| 1 | 103.0 | 86.7 | 17.0 | 12.0 |
| 2 | 80.6 | 52.8 | 19.9 | 16.2 |
| 3 | 22.7 | 0.9 | 14.9 | 3.4 |
| 4 | 2.1 | 0.0 | 5.4 | — |
| 5 | 0.0 | 0.0 | — | — |

The results shown in Table 1 and FIG. 3 indicate that mice treated with Composition A had an average wound healing time that was about 1 week less than the control mice.

The preceding merely illustrates the principles of the disclosure. All statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present disclosure, therefore, is not intended to be limited to the exemplary embodiments shown and described herein. Rather, the scope and spirit of present disclosure is embodied by the appended claims.

That which is claimed is:

1. A method for treating a wound in a subject, the method comprising:
applying a pharmaceutical composition comprising a first precursor material agent comprising fibrinogen, a second precursor material agent comprising thrombin, and silver microparticles to an abdominal incision site in an amount effective to treat the abdominal incision site.

2. The method of claim 1, wherein the first precursor material agent, the second precursor material agent and the silver particles are adapted to be combined in situ.

3. The method of claim 1, wherein the applying comprises applying the first precursor material agent prior to applying the second precursor material agent.

4. The method of claim 1, wherein the applying comprises applying the second precursor material agent prior to applying the first precursor material agent.

5. The method of claim 1, wherein the silver microparticles are spherical.

6. The method of claim 1, wherein the silver microparticles have an average diameter of 5 µm or more.

7. The method of claim 6, wherein the silver microparticles have an average diameter of 200 µm or more.

8. The method of claim 1, wherein the pharmaceutical composition comprises 25 mg/mL silver particles.

9. The method of claim 1, wherein the pharmaceutical composition comprises 250 mg/mL silver particles.

10. A pharmaceutical composition for treating a wound in a subject, the composition comprising:
a fibrin glue and silver microparticles in an amount effective to treat an abdominal incision site.

11. The pharmaceutical composition of claim 10, wherein the silver particles are spherical.

12. The pharmaceutical composition of claim 10, wherein the silver microparticles have an average diameter of 5 µm or more.

13. The pharmaceutical composition of claim 12, wherein the silver microparticles have an average diameter of 200 µm or more.

14. The pharmaceutical composition of claim 10, wherein the pharmaceutical composition comprises 25 mg/mL silver particles.

15. The pharmaceutical composition of claim 10, wherein the pharmaceutical composition comprises 250 mg/mL silver particles.

16. A device for applying a pharmaceutical composition for treating a wound in a subject, the device comprising:
a sterile container containing a first precursor material agent comprising fibrinogen, a second precursor material agent comprising thrombin, and silver microparticles in an amount effective to treat an abdominal incision site.

17. The device of claim 16, wherein the sterile container comprises a first chamber containing the first precursor material agent, a second chamber containing the second precursor material agent, and a third chamber containing the silver microparticles.

18. The device of claim 16, wherein the sterile container comprises a syringe.

19. A kit comprising:
a sterile container containing a first precursor material agent comprising fibrinogen, a second precursor material agent comprising thrombin, and silver microparticles in an amount effective to treat an abdominal incision site; and
a sealed package configured to maintain the sterility of the sterile container.

* * * * *